US00PP20504P2

(12) United States Plant Patent
Jandrew

(10) Patent No.: US PP20,504 P2
(45) Date of Patent: Nov. 24, 2009

(54) ***PENSTEMON* PLANT NAMED 'PENI PINA09'**

(50) Latin Name: *Penstemon hartwegii benth*
Varietal Denomination: Peni Pina09

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/229,275

(22) Filed: Aug. 21, 2008

(51) Int. Cl.
*A01H 5/00* (2006.01)

(52) U.S. Cl. ..... Plt./465

(58) Field of Classification Search ..... Plt./263, Plt./465

See application file for complete search history.

*Primary Examiner*—Annette H. Para
*Assistant Examiner*—Susan B McCormick Ewoldt
(74) *Attorney, Agent, or Firm*—S. Matthew Edwards

(57) ABSTRACT

A new *Penstemon* plant named 'Peni Pina09,' particularly distinguished by the large, white flower color with a vivid red-purple margin, upright and semi-compact plants, strong stems, and earlier flowering habit.

1 Drawing Sheet

Latin name of the genus and species of the plant claimed: *Penstemon hartwegii benth.*

Varietal denomination: 'Peni Pina09'.

BACKGROUND OF THE NEW PLANT

The present invention comprises a new *Penstemon*, botanically known as *Penstemon hartwegii*, and hereinafter referred to by the variety name 'Peni Pina09.'

'Peni Pina09' is a product of a planned breeding program. The new cultivar 'Peni Pina09' has large, white flower color with a vivid red-purple margin, upright and semi-compact plants, strong stems, and earlier flowering habit 'Peni Pina09' originated from a hybridization in a controlled breeding program in Gilroy, Calif. USA. The female parent was an unpatented hybrid seedling identified as '104-1' with apple blossom flower color. '104-1' is later to flower and has a taller, less compact plant habit, with fewer branches than 'Peni Pina09.'

The male parent of 'Peni Pina09' was an unpatented hybrid seedling identified as '125-3' with white and a red throat. '125-3' is later to flower and has a taller, less compact plant habit with fewer branches than 'Peni Pina09.'

'Peni Pina09' was selected as one flowering plant within the progeny of the stated cross in 2006 in a controlled environment in Gilroy, Calif. USA.

The first act of asexual reproduction of 'Peni Pina09' was accomplished when vegetative cuttings were taken from the initial selection in the April 2006 in a controlled environment in Gilroy, Calif. USA. The pollination was made in July 2005 and the seed sowing took place in October 2005 in a controlled environment in Gilroy, Calif. USA.

Horticultural examination of plants grown from cuttings of the plant initiated in April 2006 in Gilroy, Calif. USA, and continuing thereafter, has demonstrated that the combination of characteristics as herein disclosed for 'Peni Pina09' are firmly fixed and are retained through successive generations of asexual reproduction.

'Peni Pina09' has not been observed under all possible environmental conditions. The phenotype may vary significantly with variations in environment such as temperature, light intensity and day length.

A Plant Breeder's Right for this cultivar was applied for in Canada on Dec. 24, 2007. 'Peni Pina09' has not been made publicly available more than one year prior to the filing of this application.

DESCRIPTION OF THE DRAWING

The accompanying photographic drawing shows typical flower and foliage characteristics of 'Peni Pina09' with colors being as true as possible with an illustration of this type. The photographic drawing shows a flowering potted plant of the new variety, and a close-up of the flowers.

DETAILED BOTANICAL DESCRIPTION

The measurements were taken in Salinas, Calif. USA, in June 2008 on plants that were growing outside, under semi-shade. Culture of these plants started in about January 2008 in a greenhouse in Gilroy, Calif. USA. The plants were about 5–6 months old.

Color Chart used: The Royal Horticultural Society Colour Chart (R.H.S.) 2001

BRIEF SUMMARY OF INVENTION

The following observations, measurements, and comparisons describe plants grown outside in Salinas, Calif. USA. The following traits have been repeatedly observed and are determined to be basic characteristics of the new variety. The combination of these characteristics distinguishes this *Penstemon* as a new and distinct variety.

TABLE 1

DIFFERENCES BETWEEN THE NEW VARIETY 'PENI PINA09' AND A SIMILAR VARIETY

| | 'Peni Pina09' | 'Pheni Pinka' (U.S. Plant Pat. No. 17,912) |
|---|---|---|
| Flowering response | Earlier | Later |
| Plant habit | More compact | Less compact |
| Flower color markings | No throat marking | Bold throat marking |
| Peduncle length | Shorter | Longer |

Plant:

*Form, growth and habit.*—Upright, semi-compact, strong branching and vigor.

*Plant height.*—27–32 cm.

*Plant height (inflorescence included).*—46–51 cm.

*Plant width.*—33–37 cm.

Foliage:

*Arrangement.*—Opposite and decussant.

*Immature, leaf color, upper surface.*—Closest to RHS 146B. Lower surface: Closest to RHS 146B.

*Mature, leaf color, upper surface.*—Closest to RHS 146A. Lower surface: Closest to RHS 146B.

*Length.*—11-5–12.8 cm.

*Width.*—3.2–3.7 cm.

*Shape.*—Lanceolate.

*Base.*—Sessile.

*Apex shape.*—Acute.

*Margin.*—Some mostly entire, others very slightly dentate.

*Texture.*—Short pubescence on both sides.

*Color of veins, upper surface.*—RHS 144B.

*Color of veins, lower surface.*—RHS 144B.

Stem:

*Number of main stems per plant.*—3–4.

*Number of leaves per branch.*—20–22.

*Color of stem.*—RHS 144A.

*Length of stem.*—26–31 cm.

*Diameter.*—0.4–0.5 cm.

*Length of internodes.*—1.5–3.0 cm.

*Texture.*—Sparse short pubescence.

Inflorescence:

*Type.*—On first flowering it appears to be a raceme, then matures to more of a thyrse with short peduncles emerging at the nodes in opposite arrangement, each peduncle bearing 2–4 flowers or buds at various stages of development; the flowers are held somewhat horizontally. Has about 8–14 flowers per raceme.

*Blooming habit.*—Intermittent; removing of spent flowers enhances development of new flowers.

*Number of inflorescences per plant.*—11–12; early terminal pinching of apices enhances formation of more racemes.

*Raceme color.*—RHS 144B.

*Raceme length.*—20–25 cm.

*Raceme texture.*—Pubescence.

*Color of peduncle.*—RHS 144B.

*Length of peduncle.*—1.0 cm.

*Diameter of peduncle.*—0.1 cm.

*Texture.*—Short pubescence.

*Color of pedicel.*—RHS 144B.

*Length of pedicel.*—0.6–0.8 cm.

*Diameter of pedicel.*—0.1 cm.

*Texture.*—Short pubescence.

Corolla:

*Form.*—Zygomorphic and single; funnel shaped with the petals fused at base, 5 free lobed, opening outward.

*Fragrance.*—None.

*Lastingness of individual florets.*—About 6–7 days.

*Horizontal diameter of floret.*—4.2–4.3 cm.

*Vertical diameter of floret.*—3.7–3.9 cm.

*Color upper lobes, upper surface.*—N155B but whiter, with wide marginal band of RHS 63B, and RHS 63A at the margin edge; fades to almost RHS 63C with RHS 63B–C at margin edge.

*Color upper lobes, lower surface.*—RHS N 155B but whiter with a hint of RHS 63C around the margin.

*Length of upper lobes.*—1.2–1.3 cm.

*Width of upper lobes.*—1.6–1.7 cm.

*Color lateral lobes, upper surface.*—Same as upper.

*Color lateral lobes, lower surface.*—Same as upper.

*Length of lateral lobes.*—1.3–1.4 cm.

*Width of lateral lobes.*—1.6–1.8 cm.

*Color lower mid-lobe, upper surface.*—Same as upper.

*Color lower mid-lobe, lower surface.*—Same as upper.

*Length of lower mid-lobe.*—1.3–1.4 cm.

*Width of lower mid-lobe.*—1.6–1.8 cm.

*Apex shape.*—Rounded.

*Margin.*—Entire.

*Petal texture.*—Pubescent; few glandular hairs.

*Corolla color, inside.*—RHS N155B but whiter; with a hint of RHS 144C basally.

*Corolla color, outside.*—RHS N155B but whiter; sometimes blushed RHS 63B to C on the top of the corolla.

*Corolla length.*—2.5 cm.

Bud (just before opening):

*Color.*—RHS 53D at the apex; RHS 53C on the top of corolla and RHS 157C at the bottom of the corolla.

*Length.*—2.0–3.0 cm.

*Width.*—1.5 cm.

*Shape.*—Oblong.

Calyx:

*Number of sepals.*—5, fused at base.

*Color of sepals.*—RHS 144B.

*Length of sepals.*—0.7–0.9 cm.

*Width of sepals.*—0.5–0.7 cm.

*Sepal shape.*—Ovate.

*Apex shape.*—Acute.

*Margins.*—Entire.

*Texture.*—Short pubescent; glandular hairs.

Reproductive organs:

*Pistil.*—1.

*Pistil length.*—2.9–3.1 cm.

*Style color.*—RHS 59B at the basal half, fading to RHS N155B but whiter at the top of the style.

*Style length.*—2.3–2.4 cm.

*Stigma color.*—Slight hue of RHS 59D.

*Number of anthers.*—5, 4 of which are fertile.

*Color of filaments.*—RHS N 155B.

*Length filaments.*—2.2–2.4 cm.

*Pollen amount.*—Abundant.

*Color of pollen.*—RHS N155B.

*Fertility/seed set.*—Not observed on this hybrid.

Disease/pest resistance: Disease resistance or susceptibility other than typical for the species has not been observed on this hybrid.

What is claimed is:

1. A new and distinct variety of *Penstemon* plant named 'Peni Pina09,' substantially as illustrated and described herein.

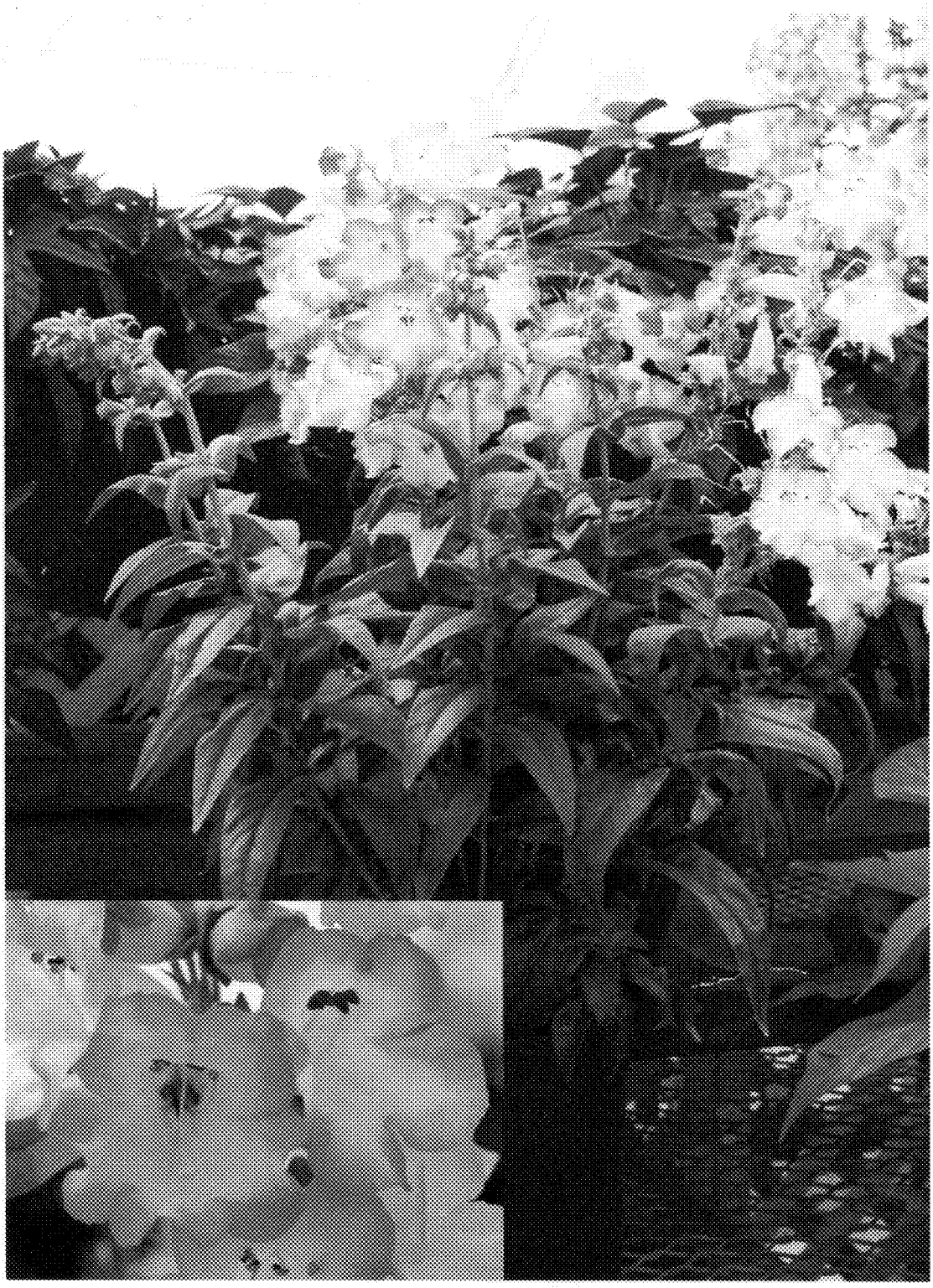

* * * * *